United States Patent [19]
Riegel et al.

[11] 4,351,819
[45] Sep. 28, 1982

[54] RECOVERY OF CHLORINE VALUES IN INTEGRATED PROCESS FOR OXYCHLORINATION AND COMBUSTION OF CHLORINATED HYDROCARBONS

[75] Inventors: Herbert Riegel, Maplewood; Chiung-Yuan Huang, Glen Ridge, both of N.J.

[73] Assignee: The Lummus Company, Bloomfield, N.J.

[21] Appl. No.: 228,463

[22] Filed: Jan. 26, 1981

[51] Int. Cl.³ .................... C01B 7/01; C07C 21/00
[52] U.S. Cl. .................... 423/488; 423/240; 423/481; 570/203; 570/224; 570/225; 570/243; 570/244
[58] Field of Search ............... 423/240, 481, 488, 502, 423/507; 570/203, 224, 225, 243, 244

[56] References Cited

U.S. PATENT DOCUMENTS

| | | | |
|---|---|---|---|
| 3,950,443 | 4/1976 | Prahl | 570/203 |
| 3,968,050 | 7/1976 | Riegel | 570/225 X |
| 3,968,200 | 7/1976 | Tsao | 423/502 X |
| 4,036,776 | 7/1977 | Riegel et al. | 423/488 X |
| 4,073,871 | 2/1978 | Optiz | 423/240 R |
| 4,113,786 | 9/1978 | Tsao | 423/488 X |
| 4,119,705 | 10/1978 | Riegel et al. | 423/507 |

Primary Examiner—Earl C. Thomas
Attorney, Agent, or Firm—Elliot M. Olstein; Louis E. Marn

[57] ABSTRACT

In an integrated process for oxychlorination and combustion of chlorinated hydrocarbons, chlorinated hydrocarbon is burned to recover chlorine values essentially as hydrogen chloride. Hydrogen chloride is recovered from the effluent from the combustion by absorption with aqueous hydrogen chloride. Hydrogen chloride recovered by the absorption is subsequently recovered and employed in an oxychlorination reaction. A gas containing hydrogen chloride, water vapor and some oxygen recovered from the oxychlorination is cooled to condense aqueous hydrogen chloride which is employed in the absorption for recovering hydrogen chloride. The remaining gas is employed in the combustion of chlorinated hydrocarbons. The process has particular applicability to an oxychlorination reaction of the type wherein a molten salt containing the higher and lower valent chlorides of a multivalent metal is contacted with hydrogen chloride and oxygen to recover hydrogen chloride by enriching the higher valent metal chloride content of the molten salt.

7 Claims, 1 Drawing Figure

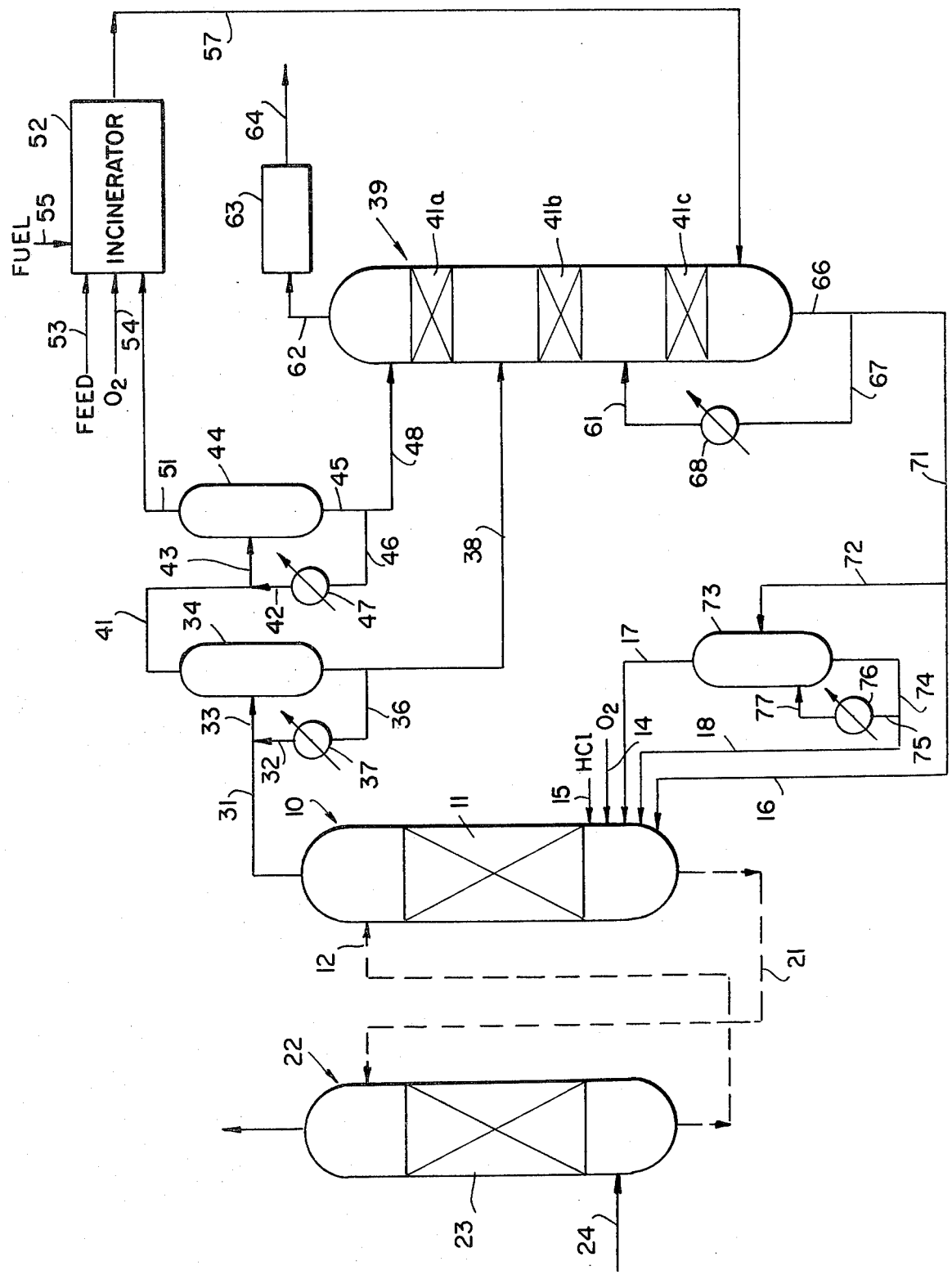

RECOVERY OF CHLORINE VALUES IN INTEGRATED PROCESS FOR OXYCHLORINATION AND COMBUSTION OF CHLORINATED HYDROCARBONS

This invention relates to recovery of chlorine values, and more particularly to recovery of chlorine values in an integrated process for oxychlorination and combustion of chlorinated hydrocarbons. Still more particularly, this invention relates to improving chlorine value recovery in a process wherein the oxychlorination involves contact of a molten salt containing the higher and lower valent chlorides of a multivalent metal with hydrogen chloride and oxygen, which is integrated with the combustion of chlorinated hydrocarbons.

Oxychlorination reactions using hydrogen chloride and oxygen are well known in the art. One type of oxychlorination reaction involves contacting a mixture of a multivalent metal chloride in both its higher and lower valent state, such as a mixture of cuprous and cupric chloride, either as an unsupported metal or supported on a suitable support, with hydrogen chloride and a molecular oxygen containing gas to increase the content of the higher valent metal chloride; e.g., cupric chloride, and in some cases also increase the oxide content of the mixture, generally as the oxychloride. Such mixture may then be employed for the chlorination of a hydrocarbon and/or partially chlorinated hydrocarbon, or for recovery of chlorine values therefrom as gaseous chlorine, or for other purposes.

Another type of oxychlorination reaction involves contacting hydrogen chloride and oxygen with the hydrocarbon or partially chlorinated hydrocarbon, generally in the presence of a suitable catalyst, to produce chlorinated hydrocarbons.

In most cases, the hydrogen chloride introduced into the oxychlorination is not completely reacted, and in such cases, the overall economics of the process may be dependent upon the effective recovery of unreacted hydrogen chloride.

Processes for recovering chlorine values from a chlorinated hydrocarbon; in particular, a chlorinated hydrocarbon which cannot be economically converted to a desired chlorinated hydrocarbon, hereinafter sometimes referred to as a waste chlorinated hydrocarbon, are also known in the art. In general, the chlorinated hydrocarbon is burned to produce a gaseous effluent which includes hydrogen chloride, and in some cases, may further include chlorine, with the chlorine values present in the combustion effluent subsequently being recovered for economic utilization thereof. Such processes also depend upon economic recovery of hydrogen chloride from the gas.

U.S. Pat. No. 3,968,200 discloses a process for recovery of chlorine values in a process which integrates combustion of chlorinated hydrocarbons with an oxychlorination reaction. In accordance with such patent, waste chlorinated hydrocarbons are burned to produce a gaseous effluent containing hydrogen chloride and chlorine, with the gaseous effluent then being contacted with a molten salt to recover chlorine values therefrom. Hydrogen chloride present in the effluent from the molten salt contacting step is then recovered by a series of quenching steps.

In accordance with the present invention there is provided a process wherein chlorinated hydrocarbon combustion is integrated with an oxychlorination reaction, and which provides for effective recovery of chlorine values. In accordance with the present invention, the chlorinated hydrocarbon is burned to produce a combustion effluent which contains the chlorine values present in the chlorinated hydrocarbon as essentially hydrogen chloride. The gaseous combustion effluent, containing hydrogen chloride, is then contacted with aqueous hydrogen chloride to recover hydrogen chloride from the gaseous effluent by absorption. Hydrogen chloride recovered by the absorption is then employed in an oxychlorination reaction. A gas recovered from the oxychlorination reaction, which contains hydrogen chloride, some oxygen and water vapor is cooled to condense aqueous hydrogen chloride, which is employed in the absorption step for recovering hydrogen chloride from the combustion effluent. In accordance with a preferred embodiment, the remaining gas is then introduced into the combustion step. In this manner, it is possible to recover the chlorine values present in the gas from the oxychlorination reaction, as well as the chlorine values present in the gas from the chlorinated hydrocarbon combustion. Furthermore, any oxygen remaining in the gas recovered from the oxychlorination is effectively utilized in the combustion. Moreover, such recovery is effected while reducing flow to the oxychlorination reaction.

The oxychlorination reactions to which the present invention are applicable are of several types and include: (1) reaction between molecular oxygen, hydrogen chloride and a salt mixture of the higher and lower valent forms of a multivalent metal chloride to enrich the higher valent metal chloride content of the mixture, and in some cases, depending upon the amount of of oxygen employed, and depending upon the desired applications, the salt may be further enriched in oxygen, generally as the oxychloride; (2) reaction between molecular oxygen, hydrogen chloride and the hydrocarbon or a partially chlorinated hydrocarbon, generally a lower (1 to 4 carbon atoms) aliphatic hydrocarbon or partially chlorinated lower aliphatic hydrocarbon to produce a chlorinated hydrocarbon; (3) reaction between hydrogen chloride and oxygen to produce chlorine (generally referred to as a Deacon reaction, but for the purposes of this invention this reaction is considered an oxychlorination); (4) reaction between an oxychloride of the multivalent metal and hydrogen chloride to produce the higher valent metal chloride; and (5) reaction between an oxychloride of the multivalent metal, hydrogen chloride and a hydrocarbon or partially chlorinated hydrocarbon to produce a chlorinated hydrocarbon.

The present invention has particular applicability to an oxychlorination reaction of the type wherein molecular oxygen, hydrogen chloride and a salt mixture of the higher and lower valent forms of a multivalent metal chloride are reacted to enrich the higher valent metal chloride content of the mixture, with as hereinabove noted, the reaction sometimes being effected in order to also increase the oxygen content of the mixture, generally as the oxychloride. In particular, the salt mixture of the higher and lower valent forms of a multivalent chloride is employed as an unsupported molten salt mixture. Such molten salts are known in the art, and no further details in this respect are deemed necessary for a complete understanding of the invention. As generally known in the art, such multivalent metals have more than one positive valent state, and are generally the chlorides of iron, manganese, copper, cobalt or chromium, preferably copper. Such molten salt mixtures also generally include a melting point depressant, which is preferably an alkali metal chloride, or which may be other metal chlorides.

The invention will be further described with respect to an embodiment thereof illustrated in the accompanying drawing, wherein:

The drawing is a simplified schematic flow diagram of an embodiment of the invention.

It is to be understood, however, that the scope of the invention is not to be limited to such embodiment.

Referring now to the drawing, there is shown a molten salt oxychlorination reactor, schematically generally indicated as 10, which includes suitable means, such as packing, schematically designated as 11, for increasing gas liquid contact. The molten salt oxychlorination reactor is designed and operated, as known in the art, for recovering chlorine values by enriching the higher valent metal chloride content of the molten salt mixture. As particularly described, the molten salt mixture, which contains cuprous and cupric chloride, and which further includes, as a melting point depressant, potassium chloride is introduced into the reactor through line 12. It is to be understood, however, that other molten salt mixtures, as known in the art, may also be used although the salt is preferably a molten salt mixture which contains cuprous and cupric chloride. The oxidation reactor 10 is further provided with oxygen through line 14. The reactor 10 may be further provided with hydrogen chloride, in line 15, with such hydrogen chloride being either a recycle stream from another portion of the plant or fresh feed hydrogen chloride. The reactor 10 is further provided with recovered hydrogen chloride, as hereinafter described, with such recovered hydrogen chloride being either derived from the combustion of a chlorinated hydrocarbon(s) and/or hydrogen chloride recovered from the effluent withdrawn from reactor 10, as hereinafter described. Such recovered hydrogen chloride may be provided as aqueous hydrogen chloride, which generally also includes some recovered salt, in line 16, or as a combination of gaseous hydrogen chloride in line 17 and aqueous hydrogen chloride, which includes some recovered salt, in line 18.

The reactor 10 is operated in a manner such that as a result of the countercurrent contact between the molten salt introduced through line 12, the oxygen introduced through line 14 and hydrogen chloride introduced into reactor 10 through one or more of lines 15, 16, 17 and 18, hydrogen chloride is recovered by enriching the higher valent metal chloride content of the salt; namely cupric chloride. In addition, if required, the salt may also be oxidized to provide the salt with an oxygen content, namely as copper oxychloride. Chlorine may also be introduced into reactor 10 with such chlorine being recovered in the salt as cupric chloride.

The oxidation reactor 10 is generally operated at a pressure of from about 1 atm. to about 20 atms., preferably at a pressure of from about 3 atms. to about 6 atms. The Salt inlet temperature to the oxidation reactor 10 is generally from about 750° F. to about 950° F., preferably from about 770° F. to about 840° F.

The molten salt, having an enriched content of cupric chloride, and which may further include oxygen, as the oxychloride, is withdrawn from reactor 10 through line 21 for introduction into a further reactor, schematically generally indicated as 22, which also includes packing 23 for increasing gas liquid contact. The reactor 22 may utilize the molten salt, having an enriched cupric chloride content, in any one of a wide variety of ways, as known in the art. Thus, for example, chlorine values may be recovered from the molten salt, as gaseous chloride. Thus, for example, such a process is described in U.S. Pat. No. 4,119,705. In addition, chlorine can be recovered from the salt for use in the production of chlorinated hydrocarbons, as described, for example, in U.S. application Ser. No. 879,802 filed on Feb. 21, 1978, or U.S. application Ser. No. 2,687, filed on Jan. 11, 1979. In such cases, a stripping gas may be introduced into reactor 22 through line 24.

The reactor 22 may also be employed for the production of chlorinated hydrocarbons, as known in the art, in which case hydrocarbon feed and hydrogen chloride and/or chlorine are also introduced into reactor 22 through line 24. Such a process is known in the art, and no further details in this respect are deemed necessary for a complete understanding of the present invention.

The molten salt withdrawn from reactor 22 through line 12 is employed in reactor 10, as hereinabove described.

A gas, containing unreacted hydrogen chloride, water vapor, any components introduced with the hydrogen chloride and oxygen, as well as any components introduced with the oxygen; for example, nitrogen when air is employed, as well as entrained salt is withdrawn from reactor 10 through line 31, and as hereinabove described, such gas is then subjected to cooling in order to condense aqueous hydrogen chloride therefrom. As particularly hereinafter described, such recovery of aqueous hydrogen chloride from the gas in line 31 is accomplished by the use of direct contact quench cooling of the gas; however, it is to be understood that other means of cooling the gas to condense aqueous hydrogen chloride may also be employed within the spirit and scope of the invention, although quench cooling, as particularly described is preferred.

The gas in line 31 is directly contacted with aqueous hydrogen chloride in line 32 to effect direct contact quench cooling thereof, with the resulting gas liquid mixture in line 33 being introduced into a quench cooler separator, schematically generally indicated as 34. Condensed aqueous hydrogen chloride is withdrawn from separator 34 with a portion thereof being passed through line 36, which includes a suitable cooler 37 for providing the quench liquid in line 32.

The remaining portion of the condensed aqueous hydrogen chloride, in line 38, is employed in an absorber schematically generally indicated as 39, as hereinafter described. The gas withdrawn from separator 34 through line 41 is direct contact quench cooled with aqueous hydrogen chloride in line 42, and a gas liquid mixture in line 43 introduced into a quench separator, schematically generally indicated as 44. The condensed aqueous hydrogen chloride is withdrawn from separator 44 through line 45 and a first portion thereof passed through line 46, which includes a cooler 47 for providing the direct contact quench liquid in line 42. The remaining portion of the condensed aqueous hydrogen chloride in line 48 is introduced into an absorber, schematically generally indicated as 39, as hereinafter described. The condensed aqueous hydrogen chloride includes salt entrained in the effluent withdrawn from reactor 10.

Although the embodiment has been particularly described with two quench cooling stages, it is to be understood that more or less than two such stages may be employed within the spirit and scope of the present invention.

In general, aqueous hydrogen chloride is recovered from the effluent withdrawn from reactor 10 by effecting cooling of the effluent to a temperature in the order of from about 100° F. to about 200° F., at a pressure in the order of from about 5 to about 10 psig. It is to be understood, however, that such conditions are illustrative, and the selection of optimum conditions is within the scope of those skilled in the art from the teachings herein.

The gas remaining after the cooling to condense aqueous hydrogen chloride, in line 51, which contains some oxygen, some hydrogen chloride and inerts, such as nitrogen, which may have been introduced with the oxygen, is now employed in a chlorinated hydrocarbon combustion zone, schematically generally indicated as 52. The chlorinated hydrocarbon incineration or combustion zone 52 is provided with chlorinated hydrocarbons to be burned in line 53, oxygen, if required in line 54 and fuel, if required in line 55. The incineration or combustion zone 52 is operated at temperatures and pressures to burn the chlorinated hydrocarbons so as to recover the chlorine values essentially as hydrogen chloride. Thus, in accordance with the preferred operation, the combustion effluent should contain no more than about 100 ppm of chlorine. In general, the incineration zone 52 is operated at an outlet temperature in the order of from 1900° to 2300° F. in order to insure that the chlorine values are recovered essentially as hydrogen chloride. As known in the art, the chlorinated hydrocarbons which are introduced into the combustion zone 52 are generally heavier chlorinated hydrocarbons which cannot be economically reconverted to desired chlorinated product. Such heavy chlorinated hydrocarbons and the combustion thereof are known in the art, and as a result, no further details thereof are deemed necessary for a complete understanding of the present invention.

In general, the outlet of the incinerator is provided with a waste heat boiler for steam generation.

A combustion effluent is withdrawn from incinerator 52 through line 57. The combustion effluent in line 57 contains hydrogen chloride derived from combusting the chlorinated hydrocarbons introduced through line 53, as well as any hydrogen chloride present in the gas introduced into the incinerator 52 through line 51. In addition, as hereinabove described, the combustion effluent in line 57 contains less than 100 ppm of chlorine. The combustion effluent in line 57 is introduced into the bottom of absorber 39 in order to recover hydrogen chloride therefrom. As particularly shown, the absorber 39 includes three gas liquid contact zones, designated as 41a, 41b and 41c, defined by suitable gas liquid contacting devices, such as, for example, packed beds. The aqueous hydrogen chloride in line 48 is introduced into the top of zone 41a, and the aqueous hydrogen chloride in line 38 is introduced into the top of zone 41b. In addition aqueous hydrogen chloride, as hereinafter described, is introduced into the top of zone 41c through line 61. As a result of countercurrent contact between the aqueous hydrogen chloride, and the combustion effluent introduced through line 57, hydrogen chloride present in the combustion effluent is absorbed by the aqueous hydrogen chloride. The absorber is operated at conditions to recover the hydrogen chloride present in the incinerator effluent as aqueous hydrogen chloride. The top of the absorber is operated at a temperature to insure water removal and the bottom temperature is at a value to recover a 10% to 21%, by weight, hydrogen chloride solution; e.g., 200° to 250° F.

The remaining portion of the combustion effluent is withdrawn from absorber 39 through line 62, and such remaining portion is essentially free of hydrogen chloride (the effluent may contain equilibrium amounts of hydrogen chloride). In addition, such gas includes inerts such as nitrogen which are present in the effluent from oxychlorination reactor 10 and incinerator 52. The effluent in line 62 may be suitably treated, for example, in zone 63 with aqueous alkali in order to remove the remaining hydrogen chloride. The remaining gas is recovered from the zone 63 in line 64, and may be purged from the system.

Aqueous hydrogen chloride, which generally contains hydrogen chloride in an amount of from 10% to 21% is withdrawn from absorber 39 through line 66 and a portion thereof passed through line 67 which includes a cooler 68 for introduction into the absorber through line 61.

The remaining portion in line 71, which generally also includes some salt which was entrained in the effluent from oxychlorination reactor 10, depending upon the heat requirements and balance of oxychlorination reactor 10, may be directly introduced into the oxychlorination reactor 10 through line 16. In some cases, however, the introduction of aqueous hydrogen chloride through line 16 will upset the heat balance of the oxychlorination reactor 10, and in such cases all or a portion of the aqueous hydrogen chloride in line 71 may be passed through line 72 for introduction into a vaporizer, schematically generally indicated at 73 wherein the aqueous hydrogen chloride is heated to effect vaporization of at least a portion thereof. Such vaporized aqueous hydrogen chloride is withdrawn from the vaporizer 73 through line 17 for introduction into the oxychlorination reactor 10. The unvaporized portion, which is withdrawn from vaporizer 73 through line 74 is introduced into the oxychlorination reactor 10 through line 18. A portion of the material in line 74 is passed through line 75 which includes a suitable heater 76 for introduction into the vaporizer 73 through line 77 to thereby provide the heat requirements for the vaporization.

Thus, in accordance with the disclosed embodiment, chlorine values are effectively recovered from a waste chlorinated hydrocarbon, as hydrogen chloride, and such hydrogen chloride is recovered by the use of a molten salt for subsequent recovery as chlorine and/or utilization in a process requiring chlorine values, without the necessity of increasing the total flow requirements to the oxychlorination reactor 10. In addition, oxygen values present in the effluent from oxychlorination reactor 10, in line 31, are ultimately utilized by introducing the gas into the incinerator 52. Furthermore, hydrogen chloride present in the effluent in line 31 from oxychlorination reactor 10 is recovered for utilization in the oxychlorination reactor 10 simultaneously with recovery of hydrogen chloride produced from the combustion of waste chlorinated hydrocarbons.

Although the invention has been described with respect to a particular embodiment thereof, it is to be understood that the scope of the invention is not to be limited thereby. Thus, for example, the oxychlorination reactor 10 could be a reactor for effecting oxychlorination other than by use of a molten salt, as particularly described.

As a further alternative, depending on the composition of the effluent in line 51, such effluent could bypass the incinerator and be introduced into absorber 39 for recovery of any remaining hydrogen chloride.

As should be apparent, the present invention has applicability to a wide variety of processes which employ molten salts in which the molten salt is oxidized (oxychlorinated) by contacting the molten salt with oxygen and hydrogen chloride, and wherein chlorine values are recovered from a chlorinated organic compound, as hydrogen chloride, by incineration, with such hydrogen chloride being subsequently utilized for the production of valuable products through the use of a molten salt. In most cases, the waste chlorinated hydrocarbons which are burned in the incinerator are those which are produced, as by-products, in the process which utilizes the molten salt; however, it is to be understood that chlorinated organics from extraneous sources may also be employed in such incinerator for recovery of chlorine values therefrom.

The present invention is particularly advantageous in that it permits effective recovery of hydrogen chloride, without the necessity of passing large volumes of gas through the oxychlorination (oxidation) reactor. In addition, oxygen values which may be present in the effluent from the oxychlorination reactor are effectively utilized in the process. Furthermore, in many cases, the gaseous effluent from the oxidizer includes some minor amounts of hydrocarbon and by passing such effluent through the incinerator such hydrocarbons are combusted thereby insuring the ultimate purging of a purer gas.

Numerous modifications and variations of the present invention are possible in light of the above teachings and, therefore, within the scope of the appended claims, the invention may be practised otherwise than as particularly described.

We claim:

1. A process for integrating recovery of chlorine values from a chlorinated organic compound by combustion with an oxychlorination reaction, the improvement comprising:
   combusting the chlorinated organic compound to recover the chlorine values therefrom essentially as hydrogen chloride;
   contacting a gaseous combustion effluent from said combusting said aqueous hydrogen chloride to recover hydrogen chloride present in the gaseous combustion effluent by absorption;
   employing hydrogen chloride recovered by the absorption in an oxychlorination reaction;
   recovering from the oxychlorination reaction a gaseous effluent containing water vapor and hydrogen chloride;
   cooling the gaseous effluent to condense aqueous hydrogen chloride, and
   employing condensed aqueous hydrogen chloride in said absorption, whereby hydrogen chloride in the effluent from both the oxychlorination and combustion are recovered for use in the oxychlorination.

2. The process of claim 1 wherein the gaseous effluent includes oxygen, a remaining gas is recovered from the cooling of the gaseous effluent and said remaining gas is employed in said combusting.

3. The process of claim 2 wherein at least a portion of the recovered hydrogen chloride is employed in the oxychlorination as aqueous hydrogen chloride.

4. The process of claim 2 wherein at least a portion of the recovered hydrogen chloride is employed in the oxychlorination as vaporized aqueous hydrogen chloride.

5. The process of claim 2 wherein the aqueous hydrogen chloride recovered by the absorption contains from 10% to 21%, by weight, hydrogen chloride.

6. The process of claim 2 wherein the combustion effluent contains less than 100 ppm chlorine.

7. The process of claim 2 wherein the oxychlorination reaction is a molten salt oxychlorination.

* * * * *